United States Patent [19]

Worthington et al.

[11] Patent Number: 4,655,820
[45] Date of Patent: Apr. 7, 1987

[54] TRIAZOLE ALKANOLS HAVING FUNGICIDAL AND PLANT GROWTH REGULATING PROPERTIES

[75] Inventors: Paul A. Worthington, Maidenhead; Patrick J. Crowley, Crowthorne; Michael B. Gravestock, Stockport, all of England

[73] Assignee: Imperial Chemical Industries Plc, London, England

[21] Appl. No.: 706,947

[22] Filed: Feb. 28, 1985

Related U.S. Application Data

[62] Division of Ser. No. 503,545, Jun. 13, 1983.

[30] Foreign Application Priority Data

Jun. 14, 1982 [GB] United Kingdom ................ 8217191
Jan. 21, 1983 [GB] United Kingdom ................ 8301677

[51] Int. Cl.$^4$ .................. A01N 43/653; C07D 249/08
[52] U.S. Cl. ............................................ 71/92; 71/76; 548/101; 548/262; 514/184; 514/383
[58] Field of Search ................ 548/101, 262; 514/184, 514/383; 71/76, 92

[56] References Cited

U.S. PATENT DOCUMENTS

| | | | |
|---|---|---|---|
| 4,414,210 | 11/1983 | Miller et al. | 548/262 X |
| 4,505,922 | 3/1985 | Jäger et al. | 548/262 X |
| 4,507,140 | 3/1985 | Sugavanam | 548/262 X |
| 4,551,469 | 11/1985 | Parry et al. | 514/383 X |
| 4,578,396 | 3/1986 | Jäger et al. | 514/383 |

Primary Examiner—Richard L. Raymond
Attorney, Agent, or Firm—Cushman, Darby & Cushman

[57] ABSTRACT

Compounds of formula:

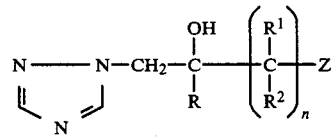

and stereo isomers thereof, wherein R is optionally substituted phenyl, alkyl or cycloalkyl and $R^1$ and $R^2$ are hydrogen or alkyl, alkenyl or alkynyl groups; Z is a straight or branched chain aliphatic group containing at least double or triple bond and optionally substituted with halogen, hydroxy, alkoxy or alkylthio; n is 1,2,3, or 4; and acid addition salts, ethers, esters and metal complexed thereof; having fungicidal and plant growth regulating activity.

5 Claims, No Drawings

TRIAZOLE ALKANOLS HAVING FUNGICIDAL AND PLANT GROWTH REGULATING PROPERTIES

This is a division of application Ser. No. 503,545 filed June 13, 1983.

This invention relates to triazole compounds useful as fungicides and plant growth regulating agents, to processes for preparing them, to fungicidal and plant growth regulating compositions containing them, and to a method of combating fungi, especially fungal infections in plants, and to a method for regulating the growth of plants using them.

The present invention provides triazole derivatives having the general formula:

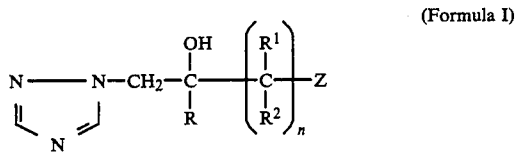
(Formula I)

and stereoisomers thereof, wherein R is optionally substituted phenyl, alkyl or cycloalkyl and $R^1$ and $R^2$ are hydrogen or alkyl, alkenyl or alkynyl groups; Z is a straight or branched chain aliphatic group containing at least one double or triple bond and optionally substituted with halogen, hydroxy, alkoxy or alkylthio; n is 1,2,3 or 4; and acid addition salts, ethers, esters and metal complexes thereof.

The group Z may be

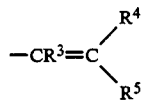

or —C≡$CR^4$ wherein $R^3$, $R^4$ and $R^5$ are hydrogen, halogen, hydroxy, alkyl, alkenyl, alkynyl, alkoxy or alkylthio.

A preferred value for n is 1 or 2.

The compounds of the invention can contain chiral centres. Such compounds are generally obtained in the form of racemic mixtures. However, these and other mixtures can be separated into the individual isomers by methods known in the art.

When any of R, $R^1$, $R^2$, $R^3$, $R^4$ and $R^5$ are alkyl it can be a straight or branched chain group having 1 to 6, e.g. 1 to 4, carbon atoms; examples are methyl, ethyl, propyl (n- or iso-propyl), butyl (n-, sec-, iso- or t-butyl), pentyl (e.g. n-pentyl) and hexyl (e.g. n-hexyl). When $R^1$ and $R^2$ are alkenyl they may be allyl and when alkynyl they may be propargyl.

R is preferably optionally - substituted phenyl and examples of suitable substituents for R when it is substituted phenyl are halogen (e.g. fluorine, chlorine or bromine), $C_{1-5}$alkyl [e.g. methyl, ethyl, propyl (n- or iso-propyl) and butyl (n-, sec-, iso-or t-butyl], $C_{1-4}$ alkoxy (e.g. methoxy and ethoxy), halo- $C_{1-4}$ alkyl (e.g. trifluoromethyl or 1, 1, 2, 2- tetrafluoroethyl), halo-$C_{1-4}$ alkoxy (e.g. trifluoromethoxy or 1, 1, 2, 2-tetrafluoroethoxy), nitro, phenyl, phenoxy, benzyl, benzyloxy (optionally ring substituted with halogen), alkylenedioxy, haloalkylenedioxy (e.g. difluoromethylenedioxy), amino, mono- or di- $C_{1-4}$ alkylamino (e.g. dimethylamino), hydroxy, morpholino and carboxy (and alkyl esters thereof). When R is cycloalkyl it may be cyclopropyl, cyclobutyl, cyclopentyl, cyclohexyl, or cycloheptyl.

Preferred values for $R^1$, $R^2$, $R^3$, $R^4$ and $R^5$ hydrogen and alkyl, especially hydrogen.

Preferred values for Z are —$CR_3$=$CH_2$ where $R_3$ is hydrogen or alkyl (especially methyl); and —C≡CH.

In a further aspect, therefore, the invention provides triazole derivatives of formula I above wherein R is phenyl or phenyl substituted with halogen, $C_{1-5}$ alkyl, $C_{1-4}$ alkoxy, halo- $C_{1-4}$ alkyl, halo $C_{1-4}$ alkoxy, nitro, phenyl, phenoxy, benzyl, benzyloxy, alkylenedioxy, haloalkylenedioxy, amino, mono- or di- $C_{1-4}$ alkylamino, hydroxy, morpholino or carboxy or alkyl esters thereof; or is straight or branched chain alkyl group having 1 to 6 especially 1 to 4, carbon atoms such as methyl, ethyl, propyl, butyl, pentyl, or hexyl; or is cycloalkyl containing from 3 to 7 carbon atoms; n is 1 or 2; and $R^1$, $R^2$, $R^3$, $R^4$ and $R^5$ are hydrogen or alkyl.

When R is substituted phenyl it may be substituted with one, two or three ring substituents as defined above. Examples of these groups are 2-, 3- or 4- chlorophenyl, 2,4- or 2,6-dichlorophenyl, 2-, 3- or 4- fluorophenyl, 2,4- or 2,6-difluorophenyl, 2-, 3- or 4- bromophenyl, 2-chloro-4-fluorophenyl, 2-fluoro-4-chlorophenyl, 2-chloro-6-fluorophenyl, 2-, 3- or 4- methoxyphenyl, 2, 4-dimethoxyphenyl, 2-, 3- or 4-ethoxy-phenyl, 2-, 3- or 4-nitrophenyl, 2-chloro-4-nitrophenyl, 2-chloro-5-nitrophenyl, 2-, 3- or 4-methylphenyl, 2, 4-dimethylphenyl, 2-, 3- or 4-t-butylphenyl, 2-, 3- or 4-trifluoromethylphenyl, 2-, 3- or 4-trifluoromethoxyphenyl, 2-, 3- or 4-(1,1,2,2-tetrafluoroethyl)phenyl, 2, 3-(difluoromethylenedioxy)phenyl, 2-fluoro-4-methoxyphenyl, 2-methoxy-4-fluorophenyl, 2-methoxy-4-chlorophenyl, 2-methoxy-4-fluorophenyl, 2-, 3- or 4-phenoxyphenyl, 2-, 3- or 4-phenylphenyl (2-, 3- or 4-biphenylyl), 2-, 3- or 4-benzylphenyl, 2-, 3- or 4-benzyloxyphenyl, 2-, 3- or 4-(4-chloro- or 4-fluorobenzyloxy)phenyl, 2-, 3- or 4-aminophenyl, 2-, 3- or 4-(N,N-dimethylamino)phenyl, 2-, 3- or 4-hydroxyphenyl, 2-, 3- or 4-carboxyphenyl, 2-, 3- or 4-(methoxycarbonyl)phenyl, and 2-, 3- or 4-morpholinophenyl.

In a still further aspect, therefore, the invention provides triazole derivatives according to formula I wherein R is phenyl, 2-, 3-, or 4- chlorophenyl, 2,4- or 2,6-dichlorophenyl, 2-, 3- or 4- fluorophenyl, 2,4- or 2,6-difluorophenyl, 2-, 3- or 4- bromophenyl, 2-chloro-4-fluorophenyl, 2-fluoro-4-chlorophenyl, 2-chloro-6-fluorophenyl, 2-, 3- or 4- methoxyphenyl, 2,4-dimethoxyphenyl, 2-, 3- or 4- ethoxyphenyl, 2-, 3- or 4- nitrophenyl, 2-chloro-4-nitrophenyl, 2-chloro-5-nitrophenyl, 2-, 3- or 4- methylphenyl, 2, 4-dimethylphenyl, 2-, 3- or 4-t-butylphenyl, 2-, 3- or 4-trifluoromethylphenyl, 2-, 3- or 4-trifluoromethoxyphenyl, 2-, 3- or 4-(1,1,2,2-tetrafluoroethyl)phenyl, 2,3-(difluoromethylenedioxy)-phenyl, 2-fluoro-4-methoxyphenyl, 2-methoxy-4-fluoro-phenyl, 2-methoxy-4-chlorophenyl, 2-methoxy-4-fluoro-phenyl, 2-, 3- or 4-phenoxyphenyl, 2-, 3- or 4-phenyl-phenyl (2-, 3- or 4-biphenylyl), 2-, 3- or 4-benzylphenyl, 2-, 3- or 4-benzyloxyphenyl, 2-, 3- or 4-(4-chloro-or 4-fluorobenzyloxy)phenyl, 2-, 3- or 4-aminophenyl, 2-, 3- or 4-(N,N-dimethylamino)phenyl, 2-, 3- or 4-hydroxyphenyl, 2-, 3- or 4-carboxyphenyl, 2-, 3- or 4-(methoxycarbonyl)phenyl, or 2-, 3- or 4-morpholinophenyl; or is or is methyl, ethyl, n- or iso-propyl, n-, sec-, iso- or t-butyl, pentyl (e.g. n-pentyl) or hexyl (e.g. n-hexyl).

The invention is illustrated by the following specific compounds set out in Table I below. These conform to the formula:

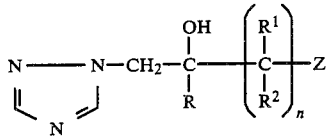

where Z may be

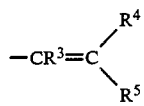

or is —CR≡CR⁴.

TABLE I

| COMPOUND | R | R¹ | R² | n | R³ | R⁴ | R⁵ | Melting Point (°C.) |
|---|---|---|---|---|---|---|---|---|
| 1 | C₆H₅ | H | H | 1 | H | H | H | 61-64° |
| 2 | 2,4-diClC₆H₃— | H | H | 1 | H | H | H | 82-84° |
| 3 | 2,4-diClC₆H₃— | H | H | 1 | CH₃ | H | H | 68-70° |
| 4 | 2,4-diClC₆H₃— | H | H | 1 | —C≡CH | | | 159-161° |
| 5 | 2,4-diClC₆H₃— | H | H | 2 | H | H | H | 125-127° |
| 6 | 2,4-diClC₆H₃— | H | H | 1 | Br | Br | H | 170-175° |
| 7 | 2,4-diClC₆H₃— | H | H | 1 | Cl | Cl | H | 149-150° |
| 8 | 2,4-diClC₆H₃— | H | H | 1 | —C≡C—I | | | 128-131° |
| 9 | 2,4-diClC₆H₃— | H | H | 1 | —C≡C—Me | | | |
| 10 | 2,4-diClC₆H₃— | H | H | 1 | H | H | Me | |
| 11 | 2,4-diClC₆H₃— | H | H | 1 | H | Me | Me | |
| 12 | 2,4-diClC₆H₃— | H | H | 2 | —C≡C—H | | | 148-150° |
| 13 | 4-ClC₆H₄ | H | H | 1 | —C≡C—H | | | 140-142° |
| 14 | 2,4-diFC₆H₃— | H | H | 1 | —C≡C—H | | | |
| 15 | 4-ClC₆H₄ | H | H | 1 | H | H | Me | |
| 16 | 4-ClC₆H₄ | H | H | 1 | —C≡C—Me | | | |

The compounds of Table I which are preferred have the structures:

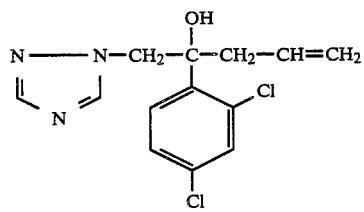

and

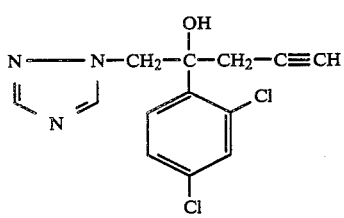

The compounds of general formula (I) may be produced by reacting a compound of general formula (II) or (III):

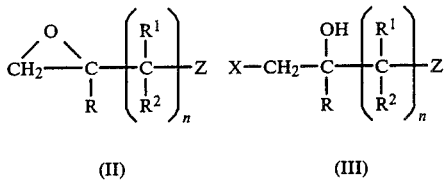

in which R, R¹, R², n and Z are as defined above and X is a halogen atom (preferably a chlorine or bromine atom), with 1,2,4-triazole either in the presence of an acid-binding agent or in the form of one of its alkali metal salts in a convenient solvent. Suitably the compound of general formula (II) or (III) is reacted at 20°-100° C. with the sodium salt of 1,2,4-triazole (the salt can be prepared by adding either sodium hydride or sodium methoxide to 1,2,4-triazole) in a convenient solvent such as acetonitrile, methanol, ethanol or dimethylformamide. The product can be isolated by pouring the reaction mixture into water and recrystallising the solid formed from a convenient solvent.

The compounds of general formula (II) and (III) can be prepared by reacting a compound of general formula (IVa) or (IVb):

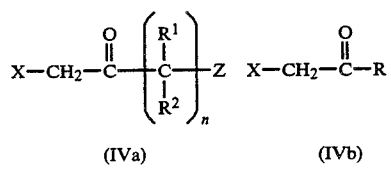

wherein R, R¹, R², n and z are as defined above and X is a halogen atom with, respectively, a Grignard compound of general formula (Va) or (Vb):

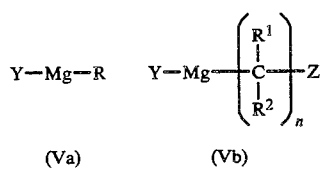

wherein R, R¹, R², n and Z are as defined above and Y is a halogen (preferably chlorine, bromine or iodine) in a convenient solvent such as diethyl ether or tetrahydrofuran. Generally a mixture of the compounds of general formula (II) and (III) are obtained.

The compounds of general formula (IV) and (V) may be made by methods set out in the literature.

The compounds of general formula (II) wherein $R^2$ is optionally substituted phenyl may also be prepared by reacting the appropriate ketone compound of general formula (VI)

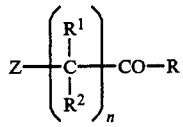
(VI)

wherein R, $R^1$, $R^2$, n and Z are as defined above, with dimethyl oxosulphonium methylide (Corey and Chaykovsky JACS, 1965, 87, 1353–1364) or dimethyl sulphonium methylide (Corey and Chaykovsky, JACS, 1962, 84, 3782) using methods set out in the literature.

The compounds of general formula (II) wherein each of R is alkyl, cycloalkyl or optionally substituted phenyl and $R^1$, $R^2$, n and Z are as defined can also be produced by reacting a β-hydroxy selenide compound of general formula (VII)

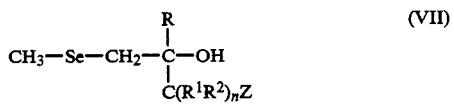
(VII)

wherein R, $R^1$, $R^2$, n and Z are as defined above, with methyl iodide in potassium t-butoxide according to the method of Van Ende, Dumont and Krief, Angew. Chem. Int. Ed., 1975, 14, 700.

The β-hydroxy selenide compound can be prepared by treating the diselenide with the appropriate ketone in the presence of butyl lithium.

The compounds of general formula (III) wherein R is alkyl or cycloalkyl and $R^1$, $R^2$, n and Z are as defined above can also be prepared by reacting a compound of general formula (VIII)

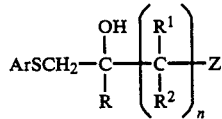
(VIII)

wherein R, $R^1$, $R^2$, n and Z are as defined above and Ar is aryl (e.g. phenyl) with an alkylating agent to give the corresponding sulphonium salt which is then reacted with 1,2,4-triazole in the form of an alkali metal (e.g. sodium or potassium) salt. The compound of general formula (VIII) can be prepared by methods known in the art.

The invention further provides, as useful intermediates, the compounds having the formulae:

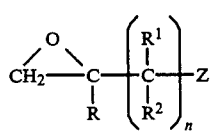
Formula (II)

and

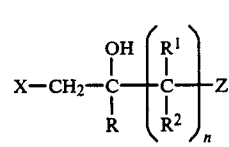
Formula (III)

wherein R, $R^1$, $R^2$, n and Z are as defined above and X is a halogen atom, especially chlorine.

The salts and metal complexes of the compounds of general formula (I) can be prepared from the latter in known manner. For example, the complexes can be made by reacting the uncomplexed compound with a metal salt in a suitable solvent.

The compounds of general formula (I) are generally prepared by the above reactions in the form of racemic mixtures. The resolution of these mixtures into the constituent enantiomers can be performed by known methods. Examples of these methods are (1) forming the diastereoisomeric salts or esters of the compound of general formula (I) with an optically active acid (e.g. camphor sulphonic acid), separating the isomeric salts or esters and converting the separated isomeric salts or esters into the enantiomers of the compound of general formula (I); (2) forming the diastereoisomeric carbamates of the compound of general formula (I) by reacting a halo-formate (e.g. chloroformate) of the latter with an optically active amine (e.g. α-methylbenzylamine), separating the isomeric carbamates, and converting the separated isomeric carbamates into the enantiomers of the compound of general formula (I), reacting the hemiphthalate with an optically active amine (e.g. α-methylbenzylamine) to give a salt of the hemiphthalate, separating the isomeric salts and converting the separated salts into the enantiomers of the compound of general formula (I); or (4) resolving the mixtures using enantio-selective crystallisation techniques (Leigh, Chemistry and Industry, 1970, pages 1016–1017, and ibid, 1977, page 36). The separation of the diastereoisomeric salts, esters and carbamates can be achieved by for example crystallisation techniques or by high pressure liquid chromatography (HPLC). Alternatively, the enantiomers can be prepared directly from the compound of general formula (II) by stereospecific reduction, for example by biochemical reduction (using for example yeast or *Aspergillus niger*) or by hydrogenation using chiral catalysts (e.g. a Wilkinson's catalyst) or by reduction with borohydride/amino acid complexes.

The compounds, salts and metal complexes are active fungicides, particularly against the diseases:

*Piricularia oryzae* on rice

*Puccinia recondita, Puccinia striiformis* and other rusts on wheat, *Puccinia hordei, Puccinia striiformis* and other rusts on barley, and rusts on other hosts e.g. coffee, apples, apples, vegetables and ornamental plants

*Erysiphe graminis* (powdery mildew) on barley and wheat and other powdery mildews on various hosts such as *Sphaerotheca fuliginea* on cucurbits (e.g. cucumber), *Podosphaera leucotricha* on apples and *Uncinula necator* on vines

*Helminthosporium* spp., *Rhynchosporium* spp. and *Pseudocercosporella herpotrichoides* on cereals

*Cercospora arachidicola* on peanuts and other Cercospora species on for example sugar beet, bananas and soya beans

*Botrytis cinerea* (grey mould) on tomatoes, strawberries, vines and other hosts

*Venturia inaequalis* (scab) on apples

Some of the compounds have also shown a broad range of activities against fungi in vitro. They have activity against various post-harvest diseases on fruit (e.g. *Penicillium digatatum* and *italicum* on oranges and *Gloeosporium musarum* on bananas). Further some of the compounds are active as seed dressings against: Fusarium spp., Septoria spp., Tilletia spp. (ie. bunt, a seed borne disease of wheat), Ustilago spp., Helminthosporium spp. on cereals, *Rhizoctonia solani* on cotton and *Corticium sasakii* on rice.

The compounds can move acropetally in the plant tissue. Moreover, the compounds can be volatile enough to be active in the vapour phase against fungi on the plant.

They may also be useful as industrial (as opposed to agricultural) fungicides, e.g. in the prevention of fungal attack on wood, hides, leather and especially paint films.

The compounds are also useful for the treatment of candidiasis and human dermatophyte infections.

The compounds, and their derivatives as defined above, also have plant growth regulating activities.

The plant growth regulating effects of the compounds are manifested as for example a stunting or dwarfing effect on the vegetative growth of woody and herbaceous mono- and di-cotyledonous plants. Such stunting or dwarfing may be useful, for example, in peanuts, cereals such as wheat and barley, oil seed rape, field beans, sunflowers, potatoes and soya bean where reduction in stem height, with or without further advantageous effects such as stem strengthening, thickening and shortening, internode shortening, increased buttress root formation and more erect stem and leaf orientation, may reduce the risk of lodging and may also permit increased amounts of fertiliser to be applied. The stunting of woody species is useful in controlling the growth of undergrowth under power lines etc. Compounds which induce stunting or dwarfing may also be useful in modifying the stem growth of sugar cane thereby increasing the concentration of sugar in the cane at harvest; in sugar cane, the flowering and ripening may be controllable by applying the compounds. Stunting of peanuts can assist in harvesting. Growth retardation of grasses can help maintenance of grass swards. Examples of suitable grasses are *Stenotaphrum secundatum* (St. Augustine grass), *Cynosurus cristatus*, *Lolium multiflorum* and *perenne, Agrostis tenuis, Cynodon dactylon* (Bermuda grass), *Dactylis glomerata*, Festuca spp. (e.g. *Festuca rubra*) and Poa spp. (e.g. *Poa pratense*). The compounds may stunt grasses without significant phytotoxic effects and without deleteriously affecting the appearance (particularly the colour) of the grass; this makes such compounds attractive for use on ornamental lawns and on grass verges. They may also have an effect on flower head emergence in for example grasses. The compounds can also stunt weed species present in the grasses; examples of such weed species are sedges (e.g. Cyperus spp.) and dicotyledonous weeds (e.g. daisy, plantain, knotweed, speedwell, thistle, docks and ragwort). The growth of non-crop vegetation (e.g. weeds or cover vegetation) can be retarded thus assisting in the maintenance of plantation and field crops. In fruit orchards, particularly orchards subject to soil erosion, the presence of grass cover is important. However excessive grass growth requires substantial maintenance. The compounds of the invention could be useful in this situation as they could restrict growth without killing the plants which would lead to soil erosion; at the same time the degree of competition for nutrients and water by the grass would be reduced and this could result in an increased yield of fruit. In some cases, one grass species may be stunted more than another grass species; this selectivity could be useful for example for improving the quality of a sward by preferential suppression of the growth of undesirable species.

The dwarfing may also be useful in miniaturising ornamental, household, garden and nursery plants (e.g. poinsettias, chrysanthemums, carnations, tulips and daffodils).

As indicated above, the compounds can also be used to stunt woody species. This property can be used to control hedgerows or to shape or reduce the need for pruning, of fruit trees (e.g. apples, pears, cherries, peaches, vines etc). Some coniferous trees are not significantly stunted by the compounds so the compounds could be useful in controlling undesirable vegetation in conifer nurseries.

The plant growth regulating effect may (as implied above) manifest itself in an increase in crop yield; or in an ability in orchards and other crops to increase fruit set, pod set and grain set.

In the potato, vine control in the field and inhibition of sprouting in the store may be possible.

Other plant growth regulating effects caused by the compounds include alteration of leaf angle and changes in leaf morphology (both of which may permit increased light interception and utilization) and promotion of tillering in monocotyledonous plants. Improved light interception is of value in all major world crops, e.g. wheat, barley, rice, maize, soya, sugarbeet, potatoes, plantation crops and orchard crops. The leaf angle effect may be useful for example in altering the leaf orientation of, for example, potato crops thereby letting more light into the crops and inducing an increase in photosynthesis and tuber weight. By increasing tillering in monocotyledonous crops (e.g. rice), the number of flowering shoots per unit area may be increased thereby increasing the overall grain yield of such crops. In addition better control and modification of hierarchical relationships is possible both in vegetative and reproductive stages of monocotyledonous and dicotyledenous plant growth, especially in cereals such as wheat, barley, rice and maize, whereby the number of flowering shoots per unit area may be increased and the size distribution of grains within the ear may be modified in such a way as to increase yield. In the treatment of rice plants, or rice crops the invention compounds can be applied, e.g. as granules or a granular formulation, for example as slow release granules, to nursery boxes, paddy water and other like cultivation loci and media. In grass swards, especially amenity grass, an increase in tillering could lead to a denser sward which may result in increased resilience in wear; and to increased yields and better quality of forage grass, e.g. improved digestability and palatability.

The treatment of plants with the compounds can lead to the leaves developing a darker green colour. In dicotyledonous plants such as soyabean and cotton, there may be promotion of sideshooting.

The compounds may inhibit, or at least delay, the flowering of sugar beet (and thereby may increase sugar yield) or otherwise modify the flowering patterns in many other crops. They may also reduce the size of sugar beet without reducing significantly the sugar yield thereby enabling an increase in planting density to be made. Similarly in other root crops (e.g. turnip, swede, mangold, parsnip, beetroot, yam and cassava) it may be possible to increase the planting density.

The compounds could be useful in restricting the vegetative growth of cotton thereby leading to an increase in cotton yield. Crop yields may also be increased by improvement of the harvest index (ie. the harvested yield as a proportion of the total dry matter produced) by altering dry matter partitioning. This applies to all the aforements root, pod cereal, tree, plantation and orchard crops.

The compounds may be useful in rendering plants resistant to stress since the compounds can delay the emergence of plants grown from seed, shorten stem height and delay flowering; these properties could be useful in preventing frost damage in countries where there is significant snow cover in the winter since then the treated plants would remain below snow cover during the cold weather. Further the compounds may cause drought or cold resistance in certain plants.

When applied as seed treatments at low rates the compounds can have a growth stimulating effect on plants.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. With the use of biodegradable polymeric slow release granules rates of 1 to 10 g per hectare are feasible; whilst electrodynamic spraying techniques may also deploy lower rates of application. However, on certain plants even application rates within these ranges may give undesired phytotoxic effects. Routine tests may be necessary to determine the best rate of application of a specific compound for any specific purpose for which it is suitable.

The compounds may be used as such for fungicidal or plant growth regulating purposes but are more conveniently formulated into compositions for such usage. The invention thus provides a fungicidal or plant growth regulating composition comprising a compound of general formula (I) as hereinbefore defined, or a salt, metal complex, ether or ester thereof, and, optionally, a carrier or diluent.

The invention also provides a method of combating fungi, which comprises applying to a plant, to seed of a plant, or to the locus of the plant or seed, a compound, or salt, metal complex, ether or ester thereof, as hereinbefore defined.

The invention also provides a method of regulating plant growth, which comprises applying to the plant, to seed of a plant or to the locus of a plant or seed, a compound, or salt, metal complex, ether or ester thereof, as hereinbefore defined.

The compounds, salts, metal complexes, ethers and esters can be applied in a number of ways, for example they can be applied, formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour; or as slow release granules. Application can be to any part of the plant, bush or tree, for example to the foliage, stems, branches or roots, or to soil surrounding the roots, or to the seed before it is planted; or to the soil generally, to paddy water or to hydroponic culture systems. The invention compounds may also be injected into plants or trees and they may also be sprayed onto vegetation using electrodynamic spraying techniques.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed space a smoke containing the compounds.

Alternatively, the compounds may be used in a microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising the compound of general formula (I) or a salt or metal complex thereof.

The compositions may also be in the form of liquid preparations for use as dips or sprays which are generally aqueous dispersions or emulsions containing the active ingredient in the presence of one or more surfactants e.g. wetting agent(s), dispersing agent(s), emulsifying agent(s) or suspending agent(s); or which are spray formulations of the kind suitable for use in electrodynamic spraying techniques. The foregoing agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), and the concentrate is to be diluted with water before use. These concentrates often should be able to withstand storage for prolonged periods and after such storage be capable of dilution with water in order to form aqueous preparations which remain homogeneous for a sufficient time to enable them to be applied by conventional and electrodynamic spray equipment. The concentrates may conveniently contain up to 95%, suitably 10–85%, for example 25–60%, by weight of the active ingredient(s). These concentrates suitably contain organic acids (e.g. of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, e.g. compounds having similar or complementary fungicidal or plant growth activity or compounds having plant growth regulating, herbicidal or insecticidal activity.

The other fungicidal compound can be, for example, one which is capable of combating ear diseases of cereals (e.g. wheat) such as Septoria, Gibberella and Helminthosporium spp., seed and soil borne diseases and downy and powdery mildews on grapes and powdery mildew and scab on apple etc. These mixtures of fungicides can have a broader spectrum of activity than the compound of general formula (I) alone; further the other fungicide can have a synergistic effect on the fungicidal activity of the compound of general formula (I). Examples of the other fungicidal compound are imazalil, benomyl, carbendazim, thiophanate-methyl, captafol, captan, sulphur, triforine, dodemorph, tridemorph, pyrazophos, furalaxyl, ethirimol, tecnazene, dimethirimol, bupirimate, chlorothalonil, vinclozolin, procymidone, iprodione, metalaxyl, forsetyl-aluminium, carboxin, oxycarboxin, fenarimol, nuarimol, fenfuram, methfuroxan, nitrotal-isopropyl, triadimefon, thiabendazole, etridiazole, triadimenol, biloxazol, dithianon, binapacryl, quinomethionate, guazatine, dodine, fentin acetate, fentin hydroxide, dinocap, folpet, dichlofluanid, ditalimphos, kitazin, cycloheximide, dichlobutrazol, a dithiocarbamate, a copper compound, a mercury compound, 1-(2-cyano-2-methoxyiminoacetyl)-3-ethyl urea, fenapanil, ofurace, propiconazole, etaconazole and fenpropemorph.

The compounds of general formula (I) can be mixed with soil, peat or other rooting media for the protection of plants against seed-borne, soil-borne or foliar fungal diseases.

Suitable insecticides are Pirimor, Croneton, dimethoate, Metasystox and formothion.

The other plant growth regulating compound can be one which controls weeds or seedhead formation, improves the level or longevity of the plant growth regulating activity of the compounds of general formula (I), selectively controls the growth of the less desirable plants (e.g. grasses) or causes the compound of general formula (I) to act faster or slower as a plant growth regulating agent. Some of these other agents will be herbicides.

Examples of suitable plant growth regulating compounds, which can display synergy in admixture, or use, with the invention compounds are the gibberellins (e.g. $GA_3$, $GA_4$ or $GA_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acids (e.g. triiodobenzoic acid), morphactins (e.g. chlorfluorecol), maleic hydrazide, glyphosate, glyphosine, long chain fatty alcohols and acids, dikegulac, fluoridamid, mefluidide, substituted quaternary ammonium and phosphonium compounds (e.g. chlormequat* chlorphonium or mepiquatchloride), ethephon, carbetamide, methyl-3,6-dichloroanisate, daminozide*, asulam, abscisic acid, isopyrimol, 1-(4-chlorophenyl)-4,6-dimethyl-2-oxo-1,2-dihydropyridine-3-carboxylic acid, hydroxybenzonitriles (e.g. bromoxynil), difenzoquat, benzoylprop-ethyl 3,6-dichloropicolinic acid, and tecnazene. Synergy will be most likely to occur with those of the foregoing which are quaternary ammonium compounds in particular those marks with an asterisk.

The use of the compounds of general formula (I) in conjunction with gibberellins can be useful where it is desired to reduce the plant growth regulating effects of the compounds (e.g. where they are to be used as fungicides). Where the compounds are being applied to the soil surrounding the plants or to the roots of the plant, the plant growth regulating effects of the compounds may possibly be reduced by using also certain types of phenoxybenzoic acids and their derivatives.

The following Examples illustrate the invention; the temperatures are given in degrees Centrigrade (°C.).

EXAMPLE 1

This Example illustrates the preparation of the compound having the formula

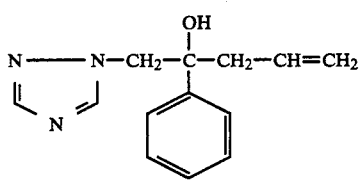

(Compound No 1 of Table I)

Stage 1. The preparation of the compound of structure

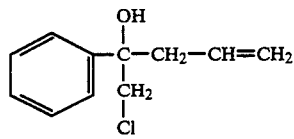

The grignard reagent allyl magnesium bromide was formed in the usual way from allyl bromide (18 g) and magnesium turnings (7.5 g) in dry ether (150 ml). ω-Chloroacetophenone (15 g) in dry ether (50 ml) was added dropwise at room temperature. After 1 hr the mixture was refluxed for 1 hr. After cooling, the ether solution was decanted from the gummy magnesium residues and poured into saturated ammonium chloride solution. The washed ethereal extract was dried over magnesium sulphate and evaporated to give a yellow liquid. The NMR and IR spectra indicated that the crude product was pure enough to be used directly for the next reaction. However it can be distilled (70°/0.01 mm) yield=6.8 g.

NMR (CDCl$_3$) δ: 2.68 (d,2H), 3.80 (s,2H), 4.90–5.20 (m,2H), 5.40–5.95 (m,1H), 7.10–7.60 (m,5H).

IR (liquid film): 3550, 3485 cm$^{-1}$.

Stage 2. The preparation of the compound

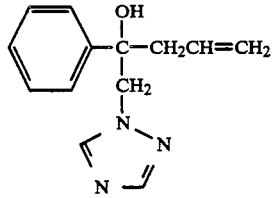

The sodium salt of 1,2,4-triazole was generated by addition of triazole (0.69 g) in dry DMF (5 ml) to a stirred suspension of sodium hydride (0.5 g of a 50% dispersion in oil) in dry DMF (30 ml). The allyl chlorohydrin from the previous reaction (1.0 g) in dry DMF (5 ml) was added and the mixture heated to 60° for 3 hr. The reaction was poured into water (100 ml) and extracted with ether (2×30 ml). After drying the ethereal extract was evaporated and a brown oil obtained, which was purified by column chromatography on silica gel eluting with ethyl acetate. This gave a clear oil which crystallised on standing to give white crystals mpt. 61°–4° C. (yield 0.45 g).

NMR (CDCl$_3$) δ: 2.44 (dd,1H), 2.80 (dd,1H), 4.16 (s,1H), 4.16 (s,1H), 4.44 (s,2H), 4.96–5.24 (m,2H), 5.40–5.90 (m,1H), 7.20–7.50 (bs,5H), 7.81 (s,1H), 7.90 (s,1H).

EXAMPLE 2

This Example illustrates the preparation of the compound having the formula:

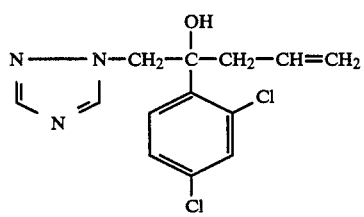

(Compound No 2 of Table I)

Stage 1. The preparation of the compounds having the formula:

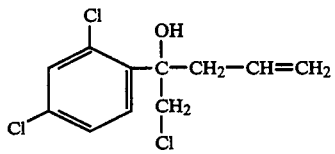

and

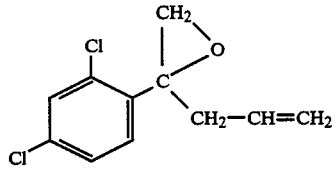

Allyl magnesium bromide was formed in the usual way from allyl bromide (5.4 g) and magnesium turnings (2.0 g) in dry ether (50 ml) at reflux and refluxing continued for 0.5 hr after addition of the bromide. The grignard solution was then carefully and rapidly decanted from excess magnesium into a pressure equalising funnel and added dropwise to a stirred solution of 2,2',4'-trichloroacetophenone (5.0 g) in dry ether (150 ml) and the rate of addition adjusted to achieve a gentle reflux. After completion of the addition, the reaction was cooled and poured into water. The ether layer was isolated, dried, and evaporated to give a yellow oil, which was chromatographed on silica gel eluting with petroleum/ether 50:50 NMR and IR suggested that the unpurified mixture could be used for the next reaction, containing chlorohydrin, epoxide and a little starting material.

Stage 2. The preparation of the compound:

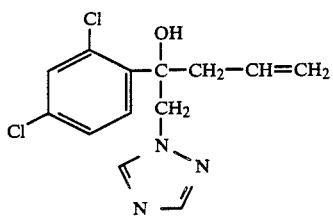

The crude product from the previous reaction was reacted with 1,2,4-triazole in the usual manner and the triazole product isolated by chromatography on silica gel eluting with ethyl acetate yield=0.16 g mp. 82°–4°.

|  |  | C | H | N |
|---|---|---|---|---|
| Microanalysis | calc | 52.34 | 4.36 | 14.09 |
|  | found | 52.03 | 4.34 | 13.73 |

NMR (CDCl$_3$) δ: 2.58 (dd,1H), 3.12 (dd,1H), 4.52 (d,1H), 4.90–5.24 (m,2H), 5.12 (d,1H), 5.40–5.84 (m,1H), 7.10 (dd,1H), 7.30 (d,1H), 7.56 (d,1H), 7.76 (s,1H), 7.92 (s,1H).

IR (nujol): 3250–3050 cm$^{-1}$.

EXAMPLE 3

This Example illustrates the preparation of the compound having the formula:

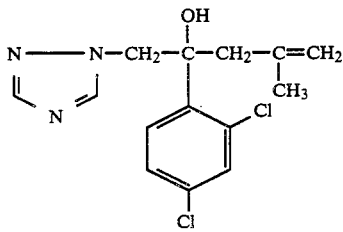

(Compound No 3 of Table I)

Stage 1. The preparation of the compounds of formula:

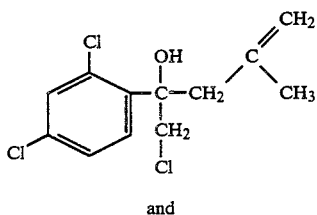

and

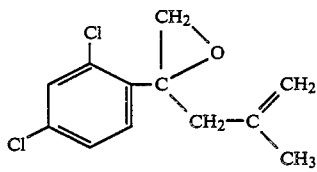

The reaction of 2-methallylmagnesium chloride (from 5.3 g methallyl chloride and 2.8 magnesium turnings) in ether with 2,2',4'-trichloroacetophenone (5.0 g) was carried out using the inverse addition procedure employed for the previous reaction of allylmagnesium bromide with the same ketone, except that after completion of the addition the mixture was refluxed for 30 mins. and stood overnight at room temperature. NMR and IR showed that the product was a mixture of the chlorohydrin and the epoxide which was used directly for the next reaction yield 2.0 g.

Stage 2. The preparation of the compound

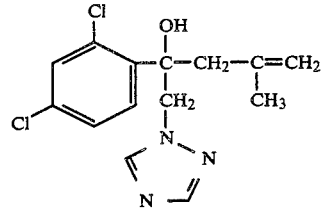

The chlorohydrin/epoxide mixture (1.5 g) was stirred at 50°–60° in dry DMF (25 ml) with the 1,2,4-triazole sodium salt (made from 1.25 g of triazole and sodium hydride 0.9 g of a 50% dispersion in oil) for 6 hours and then stood overnight at room temperature. Work-up in the usual way was followed by chromatography on silica gel eluting with ethyl acetate, to give the required product mpt. 68°–70° (0.19 g).

NMR (CDlC$_3$) δ: 1.56 (s,3H), 2.52 (d,1H), 3.15 (d,1H), 4.44 (s,1H), 4.54 (d,1H), 4.74 (s,1H), 4.84 (s,1H), 5.19 (d,1H), 7.05–7.40 (m,2H), 7.60 (d,1H), 7.80 (s,1H), 7.96 (s,1H)

IR (nujol): 3300–3100 cm$^{-1}$.

EXAMPLE 4

This Example illustrates the preparation of the compound of formula:

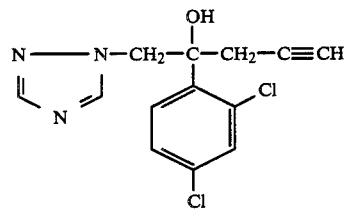

Stage 1. The preparation of the intermediate compound for formula:

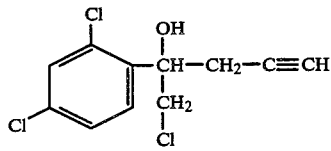

To magnesium turnings (0.70 g) in dry ether (5 ml) at 15° C. was added a few drops of propargyl bromide in dry ether. Mercuric chloride (0.025 g) was added and the mixture stirred until an exotherm was observed. The temperature was kept to about 5° C. while the rest of the bromide was added slowly (2.97 g of propargyl bromide in 20 ml dry ether, in all) and then stirred at that temperature for 1 hours. 2,2',4'-trichloroacetophenone (3.0 g) in dry THF (15 ml) was then added dropwise to the grignard solution cooled to −20°. When addition was complete the temperature was allowed to rise slowly to room temperature and stood overnight. The mixture was poured into saturated ammonium chloride solution, extracted with ether (3×20 ml), and the extract dried and evaporated to give a pale yellow liquid 3.4 g.

IR (liquid film): 3540, 3300 (sharp, strong).

Stage 2. The preparation of the compound:

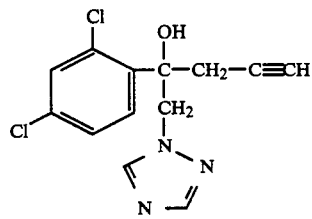

The chlorohydrin (2.0 g) was stirred with the sodium salt of triazole (from 2.1 g triazole and sodium hydride 1.45 g of 50% dispersion in oil) in dry DMF (20 ml) at 50° for 6 hours, and then stood overnight at room temperature. After work-up in the usual manner a yellow oil was obtained which crystallised on scratching in ether to give 0.23 g, mpt. 159°–61°.

NMR (CDCl$_3$ and DMSO—d$^6$) δ: 2.36 (t,1H), 2.84 (dd,1H), 3.38 (dd,1H), 3.36 (s,1H), 4.70 (d,1H), 4.92 (d,1H), 6.14 (s,1H), 7.22 (dd,1H), 7.40 (d,1H), 7.62 (d,1H), 7.68 (s,1H), 8.22 (s,1H).

EXAMPLE 5

This Example illustrates the preparation of the compound having the formula:

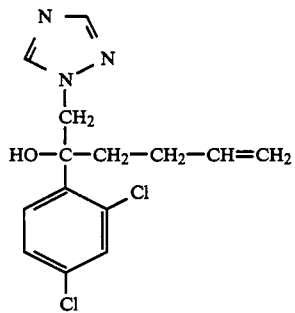

(Compound No 5 of Table I).

A solution of 1,2,4-triazole (1.2 g) in dry DMF (10 ml) was added dropwise to a suspension of sodium hydride (0.42 g of 100% material) in dry DMF (10 ml), and after completion of the addition, the reaction was stirred for 1 hour at room temperature. The epoxide (2.1 g) prepared as described below in dry DMF (10 ml) was added dropwise over a few minutes and the solution gently warmed to 60° C. for 3 hours. The reaction was cooled and poured into water, and extracted into ether. The ethereal extract was washed well with water, and then brine, and then dried over magnesium sulphate. Evaporation of the ether gave a brown oil (1.0 g). Careful trituration of the oil with ether gave a solid (350 mg) which was recrystallised (chloroform/petrol) to give the product (300 mg) mpt 125°–7° C.

NMR (CDCl$_3$) δ: 1.50–2.70 (m,4H), 4.60 (d,1H), 4.90–5.10 (m,2H), 5.24 (d,1H), 5.60–6.00 (m,1H), 7.24 (dd,1H), 7.41 (d,1H), 7.75 (d,1H), 7.90 (s,1H), 8.06 (s,1H).

IR (nujol): 3150 cm$^{-1}$.

The intermediate epoxide of

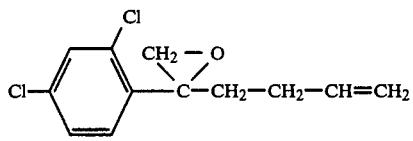

was prepared as follows:

Sodium hydride (1.0 g of 100% material) and trimethylsulphoxonium iodide were mixed, dry. Dry DMSO (50 ml) was added dropwise giving an immediate reaction. Stirring was continued at room temperature for 1.5 hours yielding a milky solution. The ketone (4.5 g, crude), prepared as described below, was added, in DMSO (10 ml) in one portion and the reaction colour became red. The solution was heated to 50 for 2 hours. The reaction was cooled and poured into water and extracted with ether. The ethereal fraction was washed well with water, dried over magnesium sulphate and evaporated to give an orange liquid (2.2 g). NMR showed the compound to be substantially pure.

NMR (CDCl$_3$) δ: 1.40–2.40 (m,4H), 2.72 (d,1H), 3.00 (d,1H), 4.80–5.10 (m,2H), 5.50–6.00 (m,1H), 7.00–7.70. (m, 3H).

The intermediate compound of formula:

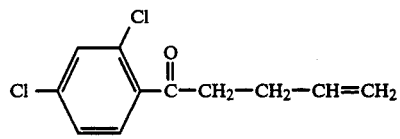

was prepared as follows:

The crude alcohol (15.0 g) was dissolved in glacial acetic acid (30 ml) and stirred at room temperature and then chilled to 15° C. Chromium trioxide (18.0 g) in water (20 ml) was added dropwise. On commencement of the addition the temperature rose to 50° C. The rate of addition was then controlled to maintain at temperature of no higher than 50° C. After stirring at 50° for 2 hours, the reaction was cooled and poured into water, extracted with ether and the ethereal extract washed with water, 2 m sodium hydroxide and then dried over MgSO$_4$. Evaporation of the solvent gave a yellow liquid (6.0 g). NMR showed this to contain about 60% of the desired product, with the remainder being 2,4-dichlorobenzaldehyde, and other impurities.

NMR (CDCl$_3$) δ: 2.3–2.6 (m,2H), 3.00 (t,2H), 4.90–5.20 (m,2H), 5.64–6.06 (m,1H), 7.20–7.50 (m,3H).

IR (liquid film): 1700 cm$^{-1}$.

The intermediate of compound of formula:

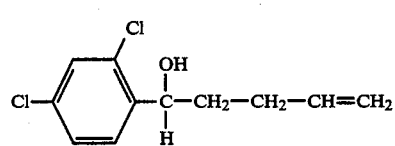

was prepared as follows:

To a solution of the grignard reagent made from 4-bromobutene (10.0 g) and magnesium metal (1.9 g) in dry ether (250 ml), stirred at room temperature, was added dropwise 2,4-dichlorobenzaldehyde (13.0 g) in dry ether (30 ml). Immediate reaction set in and the rate of addition was adjusted to maintain reflux (15 mins). After completion of the addition, the solution was refluxed for a further two hours, and then poured into dilute hydrochloric acid. The ethereal fraction was washed with water, dried over MgSO$_4$ and evaporated to yield a viscous oil (15.0 g). NMR showed this to be the desired product along with 2,4-dichlorobenzylalcohol, in proportions of about 1:1. However, this crude product was used for the next reaction.

NMR (CDCl$_3$) δ: 1.55 (m,2H), 1.9–2.3 (m,2H), 4.80–5.15 (m,2H), 5.60–6.00 (m,1H), 7.05–7.45 (m,3H).

IR (liquid film): 3350 cm$^{-1}$ (strong).

EXAMPLE 6

This Example illustrates the preparation of the compound having the structural formula:

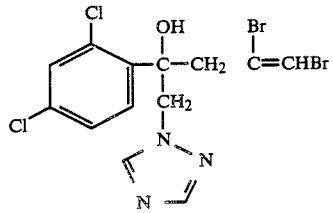

(Compound No 6 of Table I)

Bromine (0.54 g, 0.0034 m) in chloroform (5 ml) was added all at once to a stirred suspension of the alkyne (1.0 g) prepared in Example 4, in chloroform (10 ml) at room temperature. The mixture was irradiated with a 200 w tungsten lamp and the colour changed to pale orange with 2 minutes. After 15 minutes the reaction was stopped. The clear solution was poured into water containing a little sodium hydroxide, and the mixture was shaken. The chloroform layer was then washed with water, dried over magnesium sulphate and evaporated, to give a yellow oil which crystallised on standing, yield 0.32 g, (MPT 170°–175° C.). NMR analysis showed a mixture of E:Z isomers in the ratio 4:1.

NMR (CDCl$_3$) δ: 1. Peaks for E isomer: 3.15–3.90 (m,2H), 4.88 (d,1H), 5.16 (d,1H) 6.05 (s, 1H), 6.96 (s,1H), 7.35–7.90 (m,3H), 7.84 (s,1H), 8.50 (s,1H). 2. Peaks for Z isomer: 3.15–3.90 (m,2H), 4.70–5.30 (m,2H), 6.16 (s,1H), 7.04 (s,1H), 7.35–7.90 (m,4H), 8.40 (s,1H).

IR (nujol): 3150 cm$^{-1}$.

EXAMPLE 7

This Example illustrates the preparation of the compound having the structural formula

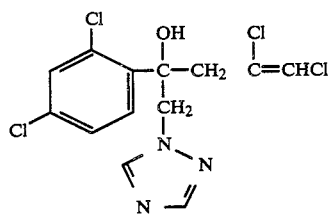

(Compound No 7 of Table I)

Chlorine (0.12 g) in chloroform (5 ml) was added to a stirred suspension of the alkyne (0.50 g) prepared in Example 4, in chloroform (5 ml) at room temperature. The mixture was irradiated with a 200 w tungsten lamp for 30 minutes. The solution was then poured into water containing a little sodium hydroxide, and the mixture was shaken. The chloroform extracts were washed with water, dried over magnesium sulphate and evaporated, to give a brown oil which crystallised on standing. The mixture was then recrystallised from petroleum/chloroform to give 0.26 g of a cream powder (mpt 149°–50° C.). NMR and GLC analysis showed the presence of only one isomer.

NMR (CDCl$_3$) δ: 3.20–3.60 (m,2H), 4.68 (d,1H), 5.32 (d,1H), 5.16 (6s,1H), 6.32 (s,1H), 7.12 (dd,1H), 7.32 (d,1H), 7.62 (d,1H), 7.76 (s,1H), 8.05 (s,1H).

IR (nujol): ν3160 cm$^{-1}$.

EXAMPLE 8

This Example illustrates the preparation of the compound having the structural formula

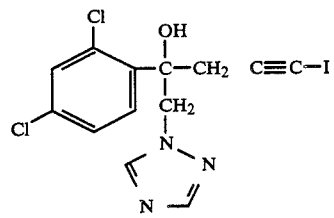

(Compound No 8 of Table I)

Morpholine (1 ml) was added to a stirred solution of iodine (0.43 g) in methanol (30 ml). The alkyne (0.25 g), prepared in Example 4, in methanol (40 ml) was then added and the mixture was stirred as a brown solution for 2 days. The methanol was evaporated, and the residue was poured into water and extracted several times with ether. The ether extracts were washed, dried over magnesium sulphate and evaporated to give a brown oil which crystallised on treatment with petroleum/ether. The solid was twice recrystallised from ether to give 100 mg of a yellow solid mpt 128°–131° C. Microanalysis and NMR confirmed the structure the compound being 90% pure. Mass spectrometry gave the correct molecular ion (422).

NMR (CDCl$_3$) δ: 3.25 (s,2H), 4.82 (d,1H), 5.26 (d,1H), 7.30 (dd, 1H), 7.48 (d,1H), 7.76 (d,1H), 7.94 (s,1H), 8.14 (s,1H).

IR (nujol): ν3120 cm$^{-1}$.

EXAMPLE 9

An emulsifiable concentrate was made up by mixing the ingredients, and stirring the mixture until all the constituents were dissolved.

Compound of Example 1: 10%
Ethylene dichloride: 40%
Calcium dodecylbenzenesulphate: 5%
"Lubrol" L: 10%
"Aromasol" H: 35%

EXAMPLE 10

A composition in the form of grains readily dispersible in a liquid, e.g. water, was prepared by grinding together the first three ingredients in the presence of added water and then mixing in the sodium acetate. The resultant mixture was dried and passed through a British Standard mesh sieve, size 44–100, to obtain the desired size of grains.

Compound of Example 2: 50%
"Dispersol" T: 25%
"Lubrol" APN5: 1.5%
Sodium acetate: 23.5%

EXAMPLE 11

The ingredients were all ground together to produce a powder formulation readily dispersible in liquids.

Compound of Example 3: 45%
"Dispersol" T: 5%
"Lissapol" NX: 0.5%
"Cellofas" B600: 2%
Sodium acetate: 47.5%

EXAMPLE 12

The active ingredient was dissolved in a solvent and the resultant liquid was sprayed on to the granules of China clay. The solvent was then allowed to evaporate to produce a granular composition.

Compound of Example 4: 5%
China clay granules: 95%

EXAMPLE 13

A composition suitable for use as a seed dressing was prepared by mixing the three ingredients.

Compound of Example 1: 50%
Mineral oil: 2%
China clay: 48%

EXAMPLE 14

A dusting powder was prepared by mixing the active ingredient with talc.

Compound of Example 2: 5%
Talc: 95%

EXAMPLE 15

A Col formulation was prepared by ball-milling the constituents set out below and then forming an aqueous suspension of the ground mixture with water.

Compound of Example 3: 40%
"Dispersol" T: 10%
"Lubrol" APN5: 1%
Water:

EXAMPLE 16

A dispersible powder formulation was made by mixing together the ingredients set out below and then grinding the mixture until all were thoroughly mixed.

Compound of Example 4: 25%
"Aerosol" OT/B: 2%
"Dispersol" A.C.: 5%
China clay: 28%
Silica: 40%

EXAMPLE 17

This Example illustrates the preparation of a dispersible powder formulation. The ingredients were mixed and the mixture then ground in a comminution mill.

Compound of Example 5: 25%
"Perminal" BX: 1%
"Dispersol" T: 5%
Polyvinylpyrrolidone: 10%
Silica: 25%
China clay: 34%

EXAMPLE 18

The ingredients set out below were formulated into a dispersible powder by mixing then griding the ingredients.

Compound of Example 5: 25%
"Aerosol" OT/B: 2%
"Dispersol" A: 5%
China clay: 68%

In Examples 9 to 18 the proportions of the ingredients given are by weight.

The remaining compounds set out in Table I above were formulated similarly to Examples 9 to 18.

There now follows an explanation of the compositions or substances represented by the various Trade Marks and Trade Names mentioned above.

LUBROL L: a condensate of nonyl phenol 1 mole) with ethylene oxide (13 moles)
AROMASOL H: a solvent mixture of alkylbenzenes
DISPERSOL T & AC: a mixture of sodium sulphate and a condensate of formaldehyde with sodium naphthalene sulphonate
LUBROL APN5: a condensate of nonyl phenol (1 mole) with naphthalene oxide (5.5 moles)
CELLOFAS B600: a sodium carboxymethyl cellulose thickener
LISSAPOL NX: a condensate of nonyl phenol (1 mole) with ethylene oxide (8 moles)
AEROSOL OT/B: dioctyl sodium sulphosuccinate
PERMINAL BX: a sodium alkyl naphthalene sulphonate

EXAMPLE 19

The compounds were tested against a variety of foliar fungal diseases of plants. The technique employed was as follows.

The plants were grown in John Innes Potting Compost (No 1 or 2) in 4 cm diameter minipots. A layer of fine sand was placed at the bottom of the pots containing the dicotyledonous plants to facilitate uptake of test compound by the roots. The test compounds were formulated either by bead milling with aqueous Dispersol T or as a solution in acetone or acetone/ethanol which was diluted to the required concentration immediately before use. For the foliage diseases, suspensions (100 ppm active ingredient) were sprayed on to the soil. Exceptions to this were the tests on *Botrytis cinerea, Plasmopara viticola* and *Venturia inaequalis*. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the diseases. An exception was the test on *Erysiphe graminis* in which the plants were inoculated 24 hours before treatment. After inoculation, the plants were put into an appropriate environment to allow infection to take place and then incubated until the disease was ready for assessment. The period between inoculation and assessment varied from four to fourteen days according to the disease and environment.

The disease control was recorded by the following grading:

4 = no disease
3 = trace—5% of disease on untreated plants
2 = 6–25% of disease on untreated plants
1 = 26–59% of disease on untreated plants
0 = 60 = 100% of disease on untreated plants The results are shown in Table II. A dash in the table thus "—" signifies that no test against the disease was conducted.

TABLE II

| COMPOUND NUMBER | PUCCINIA RECONDITA (WHEAT) | ERYSIPHE GRAMINIS (BARLEY) | PIRICULARIA ORZYAE (RICE) | PLASMOPARA INFESTANS (VINE) | PHYTOPHTHORA CINEREA (TOMATO) | BOTRYTIS CINCEREA (GRAPE BERRY) | CERCOSPORA ARACHIDICOLA (PEANUT) | VENTURIA INAEQUALIS (APPLE) |
|---|---|---|---|---|---|---|---|---|
| 1 | 4 | 4 | — | 0 | — | 4 | 4 | 4 |
| 2 | 4 | 4 | — | 0 | — | 2 | 4 | 4 |
| 3 | 4 | 4 | — | 0 | — | 2 | 4 | 4 |
| 4 | 4 | 4 | 3 | 0 | — | 0 | 4 | 4 |
| 5 | 4 | 4 | 3 | 2 | — | 1 | 4 | 4 |
| 6 | 4 | 4 | 2 | 0 | — | 0* | 4 | 4 |
| 7 | 4 | 4 | 3 | 0 | — | 0* | 4 | 4 |
| 8 | 4 | 4 | 4 | 4 | — | 0* | 4 | 4 |
| 13 | — | 4 | 3 | 0 | — | — | 4 | 4 |

*NB. These results are on *Botrytis cinerea vitis*

EXAMPLE 20

This Example illustrates the plant growth regulating properties of the compounds. The compounds were applied as an overall spray of an emulsifiable concentrate diluted to give the concentrations shown in Table III. The plants were grown in 3" pots in peat compost and sprayed at the 2 leaf stage. Plant growth regulating effects were assessed 12 days after application of the compounds. Retardation of growth was scored on a 0-3 scale where:

1 = 0-30% retardation
2 = 31-75% retardation
3 = 75% retardation

Additional plant growth regulating properties are indicated as follows:

G = darker green leaf colour
A = apical effect
T = tillering effect the compound was substantially inactive as a stunting agent.

TABLE III

| COMPOUND NUMBER | DAT | RATE (ppm) | SY | CT | SB | AT | CC | DA | WW | BR | MZ | LT | TO |
|---|---|---|---|---|---|---|---|---|---|---|---|---|---|
| 1 | 19 | 4000 | 1G | 1 | — | 1G | 1G | 1G | 1G | 1G | — | 1H | — |
| 2 | — | — | 1SF | | | | | | | | | | |
| 3 | 15 | 4000 | 1G | 3GA | 3G | 1 | 1 | 1 | T | — | 3G | 3GH | 1 |
| 4 | 15 | 3000 | 1G | 3GA | 3G | 1 | 1 | 1 | 1GT* | T | 1G | 1 | 1G |
| 5 | — | — | 1SF | | | | | | | | | | |
| 6 | 12 | — | 1 | 2GA | 2G | 1 | — | — | T | 1T | 1 | 3G | 2G |
| 7 | — | — | 1SF | | | | | | | | | | |
| 8 | — | — | 1SF | | | | | | | | | | |

Effects
G = Darker green
A = Apical
T = Tillering/sideshoots
H = Paler green
*Leaves of plant rendered erect Key to test species in Table III
SY: *Glycine max*
CT: *Gossypium hirsutum*
SB: *Beta vulgaris*
AT: *Agrostis tenuis*
CC: *Cynosurus cristatus*
DA: *Dactylis glomerata*
WW: *Triticum aestivum*
BR: *Hordeum vulgare*
MZ: *Zea mays*
LT: *Lactuca sativa*
TO: *Lycopersicon esculentum*

We claim:

1. A compound of the formula:

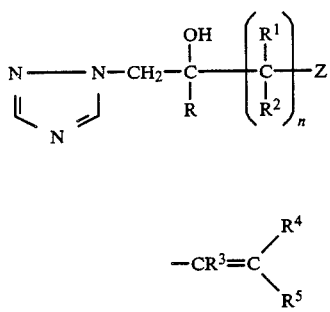

(Formula I)

wherein R³, R⁴ and R⁵ are hydrogen, halogen, hydroxy and lower alkyl, at least one of R³, R⁴ and R⁵ being halogen.

2. A compound according to claim 1 wherein R is 2,4-dichloro-phenyl; R¹ and R² are hydrogen; n is 1; and Z is

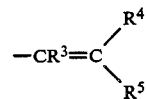

where R³ and R⁴ are bromine and R⁵ is hydrogen.

3. A compound according to claim 1 wherein R is 2,4-dichloro-phenyl; R¹ and R² are hydrogen; n is 1; and Z is

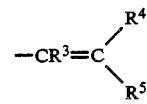

where R³ and R⁴ are chlorine and R⁵ is hydrogen.

4. A method of combating fungi, which comprises applying to a plant, to seed of a plant, or to the locus of the plant or seed, a compound, as claimed in claim 1.

5. A method of regulating plant growth, which comprises applying to the plant, to seed of a plant or to the locus of a plant or seed, a compound as claimed in claim 1.

* * * * *

UNITED STATES PATENT AND TRADEMARK OFFICE
CERTIFICATE OF CORRECTION

PATENT NO. : 4,655,820

DATED : April 7, 1987

INVENTOR(S) : Paul A. WORTHINGTON, Patrick J. CROWLEY and Michael B. GRAVESTOCK

It is certified that error appears in the above-identified patent and that said Letters Patent is hereby corrected as shown below:

Claim 1 amended by inserting:

"wherein R is phenyl or halophenyl; $R^1$ and $R^2$ are both hydrogen; n is 1, 2, 3 or 4; and Z is" between the formula appearing at column 24, lines 15-20 and the formula appearing at lines 20-24.

Signed and Sealed this

Twenty-fifth Day of August, 1987

*Attest:*

DONALD J. QUIGG

*Attesting Officer*      *Commissioner of Patents and Trademarks*